(12) United States Patent
Steele (10) Patent No.: US 9,549,760 B2
(45) Date of Patent: Jan. 24, 2017

(54) REDUCED EXTRAVASATION OF BONE CEMENT

(75) Inventor: Bradley E. Steele, Germantown, TN (US)

(73) Assignee: KYPHON SARL, Neuchatel (CH)

(*) Notice: Subject to any disclaimer, the term of this patent is extended or adjusted under 35 U.S.C. 154(b) by 1014 days.

(21) Appl. No.: 12/915,540

(22) Filed: Oct. 29, 2010

(65) Prior Publication Data

US 2012/0109139 A1    May 3, 2012

(51) Int. Cl.
| | |
|---|---|
| *A61B 17/88* | (2006.01) |
| *A61B 17/34* | (2006.01) |
| *A61B 17/70* | (2006.01) |
| *A61L 27/20* | (2006.01) |
| *A61L 24/08* | (2006.01) |

(52) U.S. Cl.
CPC .......... *A61B 17/3472* (2013.01); *A61B 17/70* (2013.01); *A61B 17/8802* (2013.01); *A61B 17/8855* (2013.01); *A61L 24/08* (2013.01); *A61L 27/20* (2013.01); *A61B 17/3421* (2013.01); *A61B 17/7098* (2013.01); *A61L 2430/02* (2013.01)

(58) Field of Classification Search
CPC A61F 2/4601; A61B 17/8802; A61B 17/8805
USPC .................................. 606/86 R, 279, 92–94
See application file for complete search history.

(56) References Cited

U.S. PATENT DOCUMENTS

| | | | |
|---|---|---|---|
| 4,708,270 A * | 11/1987 | Ruesch | ...................... 222/386.5 |
| 5,549,904 A | 8/1996 | Juergensen et al. | |
| 5,550,172 A | 8/1996 | Regula et al. | |
| 6,554,830 B1 * | 4/2003 | Chappius | ..................... 606/246 |
| 6,641,587 B2 * | 11/2003 | Scribner | ............ A61B 17/1631 604/218 |
| 7,252,672 B2 * | 8/2007 | Yetkinler et al. | ............... 606/92 |
| 8,066,713 B2 * | 11/2011 | DiMauro et al. | ............... 606/94 |
| 8,226,657 B2 * | 7/2012 | Linderman et al. | ........ 606/86 R |
| 8,361,078 B2 * | 1/2013 | Beyar et al. | .................... 606/94 |
| 8,415,407 B2 * | 4/2013 | Beyar et al. | ................... 523/117 |
| 8,540,722 B2 * | 9/2013 | Beyar et al. | ................... 606/94 |
| 2005/0256220 A1 * | 11/2005 | Lavergne et al. | ............. 523/115 |
| 2006/0041033 A1 | 2/2006 | Bisig et al. | |
| 2006/0095016 A1 | 5/2006 | Pauza et al. | |
| 2007/0186818 A1 | 8/2007 | Bohner | |
| 2009/0149954 A1 | 6/2009 | Hu et al. | |
| 2010/0070049 A1 | 3/2010 | O'Donnell et al. | |
| 2010/0091606 A1 | 4/2010 | Kwan et al. | |
| 2010/0125240 A1 | 5/2010 | Spedden et al. | |

OTHER PUBLICATIONS

PCT International Search Report, PCT/US2011/057877, May 31, 2012.

* cited by examiner

*Primary Examiner* — Anu Ramana
(74) *Attorney, Agent, or Firm* — Sorell Lenna & Schmidt LLP (57) ABSTRACT

The risk of bone cement extravaation can be reduced by delivering a calcium-dependent polymerizing sealant into a bone structure prior to delivery of bone cement into that structure. The polymerization of the sealant in response to the calcium within the bone structure can fill cracks and any other potential cement leakage paths, thereby minimizing the potential for subsequent extravaation. The benefits of the use of a calcium-dependent polymerizing sealant can be provided in any procedure involving the use of bone cement, such as spinal fixation, vertebroplasty, and kyphoplasty, among others.

18 Claims, 8 Drawing Sheets

REDUCED EXTRAVASATION OF BONE CEMENT

BACKGROUND

The invention relates generally to medical devices and procedures, and more particularly to medical devices and procedures for preventing bone cement extravasation during surgical procedures.

Bone cement is the term typically used to refer to polymethyl methacrylate (PMMA), which is commonly used to reinforce or augment bone structures. For example, bone screws are often used to stabilize bone structures within the body, such as during a spinal fracture repair procedure. Such bone screws can be implanted into the vertebral pedicle (and are therefore sometimes referred to as pedicle screws) in conjunction with other structural members, such as, for example, rods, bars and/or plates to realign and stabilize a compromised spine.

Unfortunately, after implantation into a host bone structure, bone screws can be susceptible to becoming "pulled out" from the host bone structure, loosened within the host bone structure and/or destabilized within the host bone structure. The susceptibility of a bone screw to pullout, loosening and/or destabilization can be compounded when the bone screw is implanted into soft portions of a bone structure (e.g., cancellous bone or diseased bone) and/or the bone screw is subjected to high loads.

Consequently, bone cement is frequently used to augment the pull-out strength of known bone screws. For example, fenestrated screws have been developed that include a central channel (cannulation) and multiple fenestrations along the shaft. Bone cement injected through the central channel can then be dispersed through the fenestrations into the surrounding bone, thereby providing a reinforced structure that can enable more secure fixation of the screw.

However, the use of bone cement in such procedures introduces additional risks—in particular the risks associated with extravasation of the bone cement from the bone environment. The polymerization of PMMA is an exothermic reaction that can cause necrosis of adjacent cells. In addition, PMMA exhibits toxicity that can cause pulmonary embolism or neurologic deficit if allowed to come into contact with vessels or nerves. This extravasation risk is present in other procedures that make use of bone cement, such as vertebroplasty and kyphoplasty.

Accordingly, it is desirable to provide systems and methods for minimizing the risk of extravasation during surgical procedures involving the use of bone cement.

SUMMARY

By applying a calcium-dependent polymerizing sealant (e.g., sodium alginate) to a target bone structure prior to delivery of bone cement, leakage paths for the bone cement can be blocked, thereby beneficially preventing bone cement extravasation.

In one embodiment, the delivery of bone cement for enhancing screw retention can be preceded by delivery of a calcium-dependent polymerizing sealant into the bone structure. In some embodiments, delivery of the sealant and/or the bone cement can be performed via fenestrations in the bone screw(s).

In another embodiment, vertebroplasty can involve delivery of a calcium-dependent polymerizing sealant prior to injection of bone cement into a vertebral body. In various embodiments, the injection of the sealant and the bone cement can be performed through the same or different needles.

In another embodiment, kyphoplasty can involve delivery of a calcium-dependent polymerizing sealant into a preformed cavity in a vertebral body prior to delivery of bone cement into the cavity. In various embodiments, the sealant and the bone cement can be delivered through the same or different delivery nozzles.

In various other embodiments, a surgical kit can include a system for performing a surgical procedure within bone, a quantity of calcium-dependent polymerizing sealant, and instructions for using the calcium-dependent polymerizing sealant with the system. In various embodiments, the system can include a bone screw, a vertebroplasty needle, or a cavity creation device for kyphoplasty, among other types of instruments/hardware.

As will be realized by those of skilled in the art, many different embodiments of methods and systems for sealing leakage paths in bone prior to bone cement delivery according to the present invention are possible. Additional uses, advantages, and features of the invention are set forth in the illustrative embodiments discussed in the detailed description herein and will become more apparent to those skilled in the art upon examination of the following.

DETAILED DESCRIPTION

By applying a calcium-dependent polymerizing sealant (e.g., sodium alginate) to a target bone structure prior to delivery of bone cement, leakage paths for the bone cement can be blocked, thereby beneficially preventing bone cement extravasation.

Figure 1A:
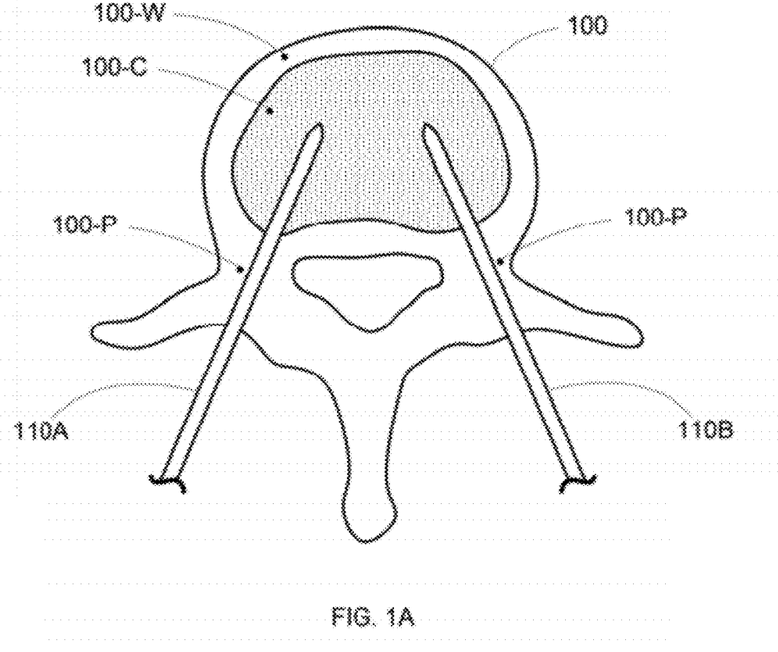
FIGS. 1A-1D show an exemplary pedicle screw placement procedure incorporating the use of a calcium-dependent polymerizing sealant.

FIGS. 1A-1D show an exemplary insertion of fixation devices into a bone involving the use of bone cement for enhancement of retention. FIG. 1A shows a transverse cross section of a vertebral body 100. Vertebral body 100 includes cortical bone 100-W surrounding cancellous bone 100-C. Note that while a human vertebra is depicted and described herein for exemplary purposes, in various other embodiments, vertebral body 100 could be replaced with any other type of bone, an animal bone (e.g., for a veterinary procedure), or even a cadaveric bone or artificial bone (e.g., for a training or test procedure).

In FIG. 1A, path creation structures 110A and 110B (e.g., guidewires, drills and/or osteotomes) are used to penetrate the pedicles 100-P of vertebral body 100 and provide a passage to cancellous bone 100-C. Note that in various embodiments, path creation structures 110A and 110B can represent multiple instruments (e.g., guidewire followed by drill).

Figure 1B:
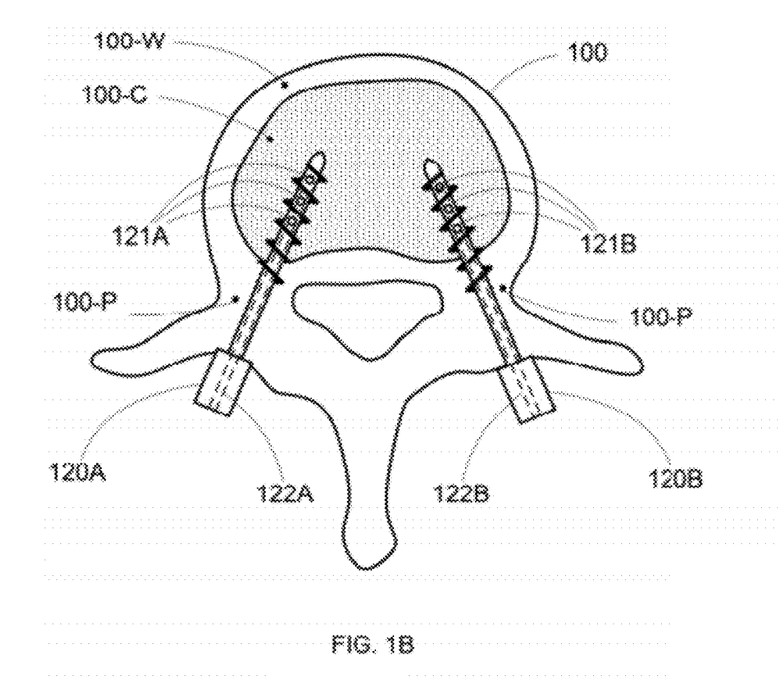

Then, in FIG. 1B, bone screws 120A and 120B are inserted into vertebral body 100 via pedicles 100-P. Bone screws 120A and 120B include fenestrations 121A and 121B, respectively, which provide delivery paths for material provided via internal cannulations (channels) 122A and 122B, respectively, within bone screws 120A and 120B, respectively.

Figure 1C:
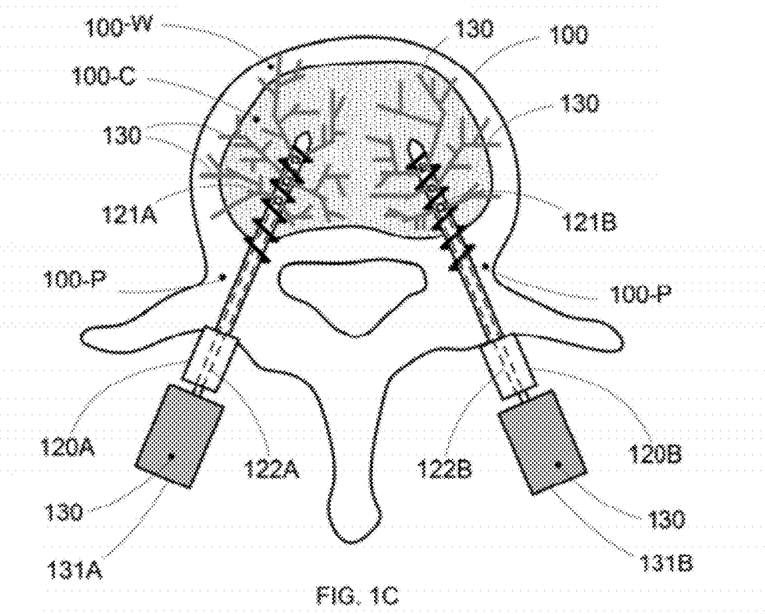

Next, in FIG. 1C, a calcium-dependent polymerizing sealant 130 is introduced into vertebral body 100 via bone screws 120A and 120B. Sealant 130 can include any type of material that thickens and/or stiffens in response to calcium and can be delivered into the cracks and crevices of a bone structure.

For example, in one embodiment, sealant 130 can include sodium alginate, which polymerizes in response to calcium ions, such as those present in bone structures. Alginate is formed from two homopolymeric blocks of (1-4)-linked β-D-mannuronate (M) and α-L-guluronate (G)—the relative concentration of M:G can alter the stiffness of the calcium dependent cross-linking/polymerization.

In some embodiments, the M:G ratio can be selected based on the desired properties of the resulting polymer. For example, a high M:G ratio can result in a more elastic polymer that may be effective in sealing irregular or larger gaps and openings, whereas a low M:G ratio can result in a stiffer polymer that may be effective in sealing more porous bone constructions. Note, however, that such selections are highly situation-specific, and in many instances a low M:G ratio may be desirable for sealing larger openings, and a high M:G ratio may be desirable for sealing densely populated passages.

Note further that in some embodiments, sealant 130 can be a multi-part substance, in which the components can be mixed prior to delivery into the bone structure, or can be delivered sequentially or simultaneously into the bone structure. For example, in one embodiment, sealant 130 can include a calcium injection that is delivered into vertebral body 100 prior to, or after, delivery of an alginate, whereby the injected calcium encourages more complete polymerization of the alginate.

To introduce sealant 130 into vertebral body 100, delivery systems 131A and 131B are coupled to bone screws 120A and 120B, respectively. Delivery systems 131A and 131B can be any systems for delivering sealant 130, including syringes, high pressure injection systems (e.g., hydraulic pumps, pressurized systems, mechanical linkages/screw systems), and/or automated feed systems, among others.

Sealant 130 from delivery systems 131A and 131B is then urged through cannulations 122A and 122B, respectively, and out fenestrations 121A and 121B, respectively, into vertebral body 100. Sealant 130 flows into vertebral body 100, filling cracks and crevices within cancellous bone 100-C and/or cortical bone 100-W. Specifically, the calcium within vertebral body 100 causes sealant 130 to polymerize and thicken, and thereby provide the desired gap-filling within vertebral body 100.

Figure 1D:
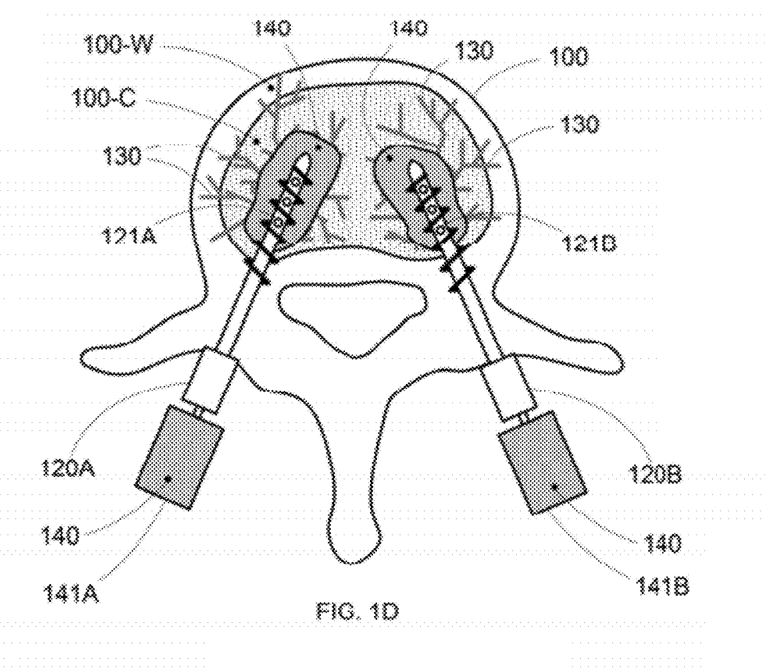

Once the desired sealing of vertebral body 100 has been achieved, bone cement 140 can be delivered into vertebral body 100 to provide a secure engagement structure for bone screws 120A and 120B, as shown in FIG. 1D. In particular, delivery systems 141A and 141B are coupled to bone screws 120A and 120B, respectively. In some embodiments, delivery systems 141A and 141B can be the same as delivery systems 131A and 131B, respectively (e.g., the same high pressure injection system(s) but coupled to a reservoir(s) of bone cement 140, or a two-chamber syringe(s), among others). In various other embodiments, delivery systems 141A and 141B can be separate (and optionally different) delivery systems (e.g., a manual syringe for the lower viscosity sealant 130 and a high pressure injection system for the higher viscosity bone cement 140).

In any event, bone cement 140 from delivery systems 141A and 141B is urged through cannulations 122A and 122B, respectively, and out fenestrations 121A and 121B, respectively, into vertebral body 100. Because cracks and other potential external passageways in vertebral body 100 have been filled by sealant 130, bone cement 140 largely remains in the region around bone screws 120A and 120B, thereby minimizing the risk of bone cement extravasation.

To facilitate the above-described procedure, in some embodiments, a bone screw kit can be provided that includes bone screws 120A and 120B, a quantity of sealant 130, and instructions for using sealant 130 with bone screws 120A and 120B. In various other embodiments, the kit can include additional hardware/instruments, such as guidewires, drills, drivers, delivery systems, and/or bone cement.

Figure 2A:
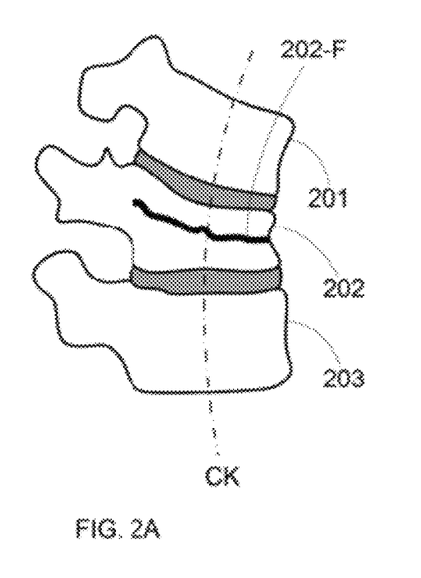
FIGS. 2A-2D show an exemplary vertebroplasty procedure incorporating the use of a calcium-dependent polymerizing sealant.

The benefits of the bone sealing operation described above can be beneficially applied to any procedure involving the use of bone cement. For example, FIGS. 2A-2D show an exemplary vertebroplasty procedure, in which bone cement is injected into a fractured vertebra to stabilize a damaged or weakened spine. FIG. 2A shows a portion of a human spinal column having vertebral bodies 201, 202, and 203. Note that while vertebral bodies 201, 202, and 203 are depicted and described as being part of a human spine for exemplary purposes, in various other embodiments, vertebral bodies 201, 202, and 203 can be animal bones (e.g., for veterinary procedures), or cadaveric/artificial bones (e.g., for training or test procedures).

Vertebral body 202 has collapsed due to a vertebral compression fracture (VCF) 202-F that could be the result of osteoporosis, cancer-related weakening of the bone, and/or physical trauma. VCF 202-F creates an abnormal curvature CK of the spine that can lead to severe pain and further fracturing of adjacent vertebral bodies.

In one embodiment, rather than immediately injecting fractured vertebral body 202 with bone cement, vertebral body 202 can be injected with a calcium-dependent polymerizing sealant 230 (similar to sealant 130 described with respect to FIGS. 1A-1D, such as a sealant including sodium alginate). In particular, a needle 220 (e.g., straight, curved, flexible, and/or steerable needle) is positioned within vertebral body 202, either via direct insertion or in conjunction with additional instruments (e.g., a guidewire). In some embodiments, a cannula can be used to provide an access path to vertebral body 202.

Figure 2B:
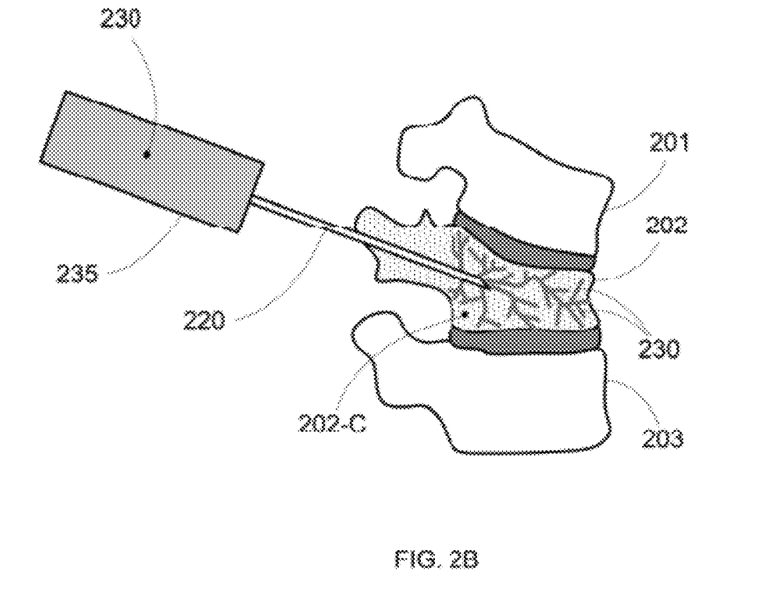

A delivery system 235 coupled to needle 220 is then used to deliver sealant 230 to vertebral body 202. Delivery system 235 can be any system for delivering sealant 230, including a syringe, a high pressure injection system (e.g., hydraulic pump, pressurized system, mechanical linkage/screw system), and/or an automated feed system, among others.

Sealant 230 flows into vertebral body 202, filling cracks and crevices within the cancellous bone 202-C and/or the cortical bone of vertebral body 202. Specifically, the calcium within vertebral body 202 causes sealant 230 to polymerize and thicken, and thereby provide the desired gap-filling within vertebral body 202.

Figure 2C:
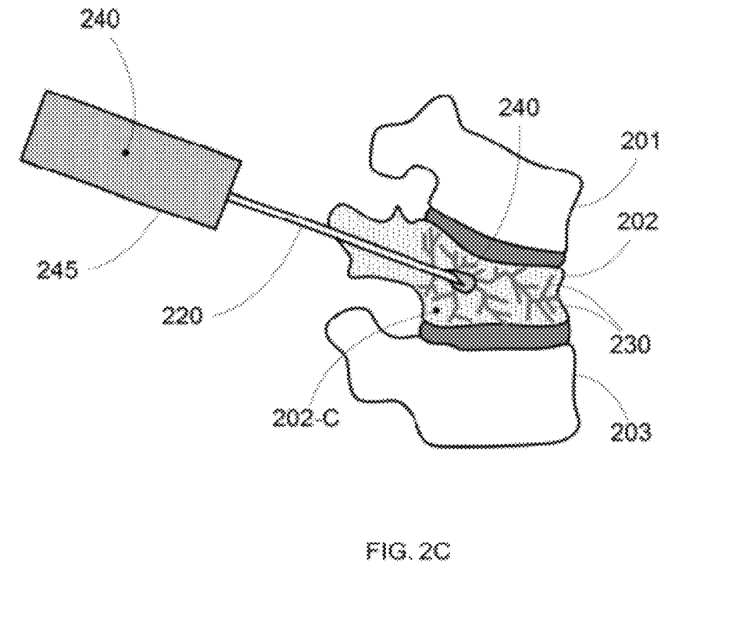

Once the desired sealing of vertebral body 202 has been achieved, bone cement 240 can be delivered into vertebral body 202, as shown in FIG. 2C. In particular, a delivery system 245 can be coupled to needle 220 to urge bone cement 240 through needle 220 into vertebral body 202.

In some embodiments, delivery system 245 can be the same as delivery system 235 (e.g., the same high pressure injection system but coupled to a reservoir of bone cement 240, or a two-chamber syringe, among others). In various other embodiments, delivery system 245 can be a separate (and optionally different) delivery system (e.g., a syringe for the lower viscosity sealant 230 and a high pressure injection system for the higher viscosity bone cement 240).

Note further that in some embodiments, both delivery systems 235 and 245 can deliver sealant 230 and bone cement 240, respectively, through the same needle 220. In other embodiments, different needles 220 can be used with delivery systems 235 and 245.

Figure 2D:
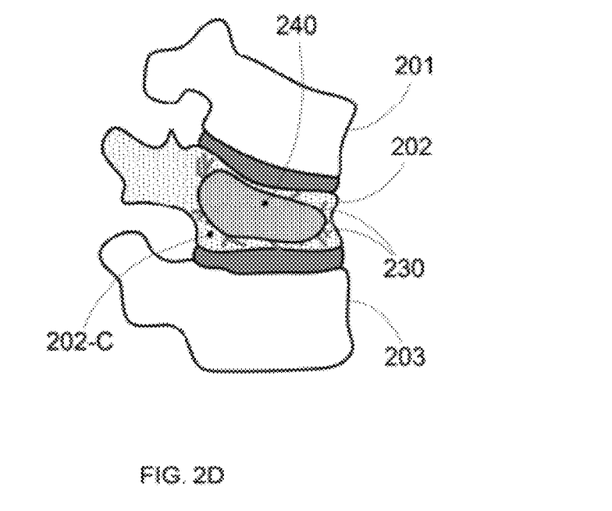

In any event, because cracks and other potential external passageways in vertebral body 202 have been filled by sealant 230, bone cement 240 can be contained within vertebral body 202, thereby minimizing the risk of bone cement extravasation. This can be particularly beneficial with respect to vertebroplasty, due to the high cement delivery pressures and relatively low viscosity bone cement delivery states used in the procedure. Once a desired amount of bone cement 240 is delivered into vertebral body 202, needle 220 can be removed, leaving vertebral body 202 reinforced and stabilized by the hardened bone cement 240.

To facilitate the above-described procedure, in some embodiments, a vertebroplasty kit can be provided that includes needle 220, a quantity of sealant 230, and instructions for using sealant 230 with needle 220. In various other embodiments, the kit can include additional hardware/instruments, such as guidewires, drills, drivers, delivery systems, and/or bone cement.

Kyphoplasty is another VCF-treatment option that addresses many of the issues associated with vertebroplasty. In a kyphoplasty procedure, a defined cavity is created within the fractured vertebral body to receive and contain the subsequently delivered bone cement. The cavity creation operation of kyphoplasty can also restore some or all of the original height of the vertebral body, thereby further enhancing the benefit of the procedure.

Figure 3A:
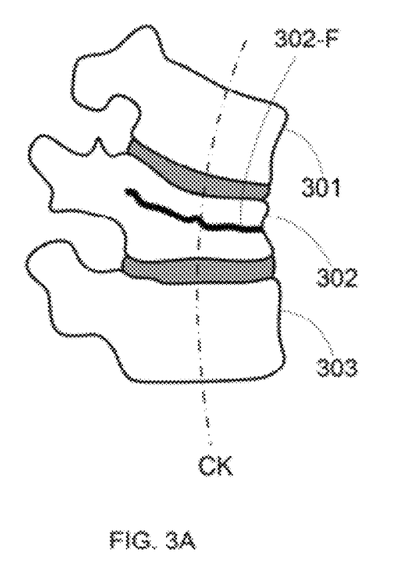
FIGS. 3A-3G show an exemplary kyphoplasty procedure incorporating the use of a calcium-dependent polymerizing sealant.

FIGS. 3A-3G show an exemplary kyphoplasty procedure that incorporates the use of a sealant to minimize the risk of bone cement extravasation. FIG. 3A shows a portion of a human vertebral column having vertebral bodies 301, 302, and 303. Note that while vertebral bodies 301, 302, and 303 are depicted and described as being part of a human spine for exemplary purposes, in various other embodiments, vertebral bodies 301, 302, and 303 can be animal bones (e.g., for veterinary procedures), or cadaveric/artificial bones (e.g., for training or test procedures).

Vertebral body 302 has collapsed due to a vertebral compression fracture (VCF) 302-F that could be the result of osteoporosis, cancer-related weakening of the bone, and/or physical trauma. VCF 302-F creates an abnormal curvature CK of the spine that can lead to severe pain and further fracturing of adjacent vertebral bodies.

Figure 3B:
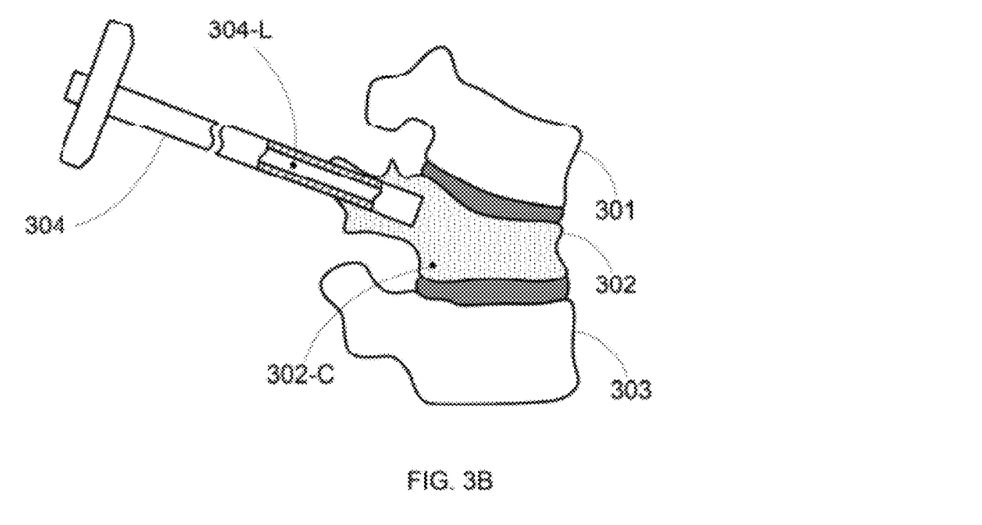

FIG. 3B shows a cannula 304 being positioned next to the target surgical location, which in this case is the cancellous bone structure 302-C within fractured vertebra 302. In this manner, a percutaneous path to vertebra 302 is provided via an interior lumen 304-L of cannula 304. Typically, cannula 304 is docked into the exterior wall of the vertebral body (using either a transpedicular or extrapedicular approach) using a guide needle and/or dissector, after which a drill or other access tool (not shown) is used to create a path further into the cancellous bone 302-C of vertebra 302. However, any other method of cannula placement can be used to position cannula 304.

Figure 3C:
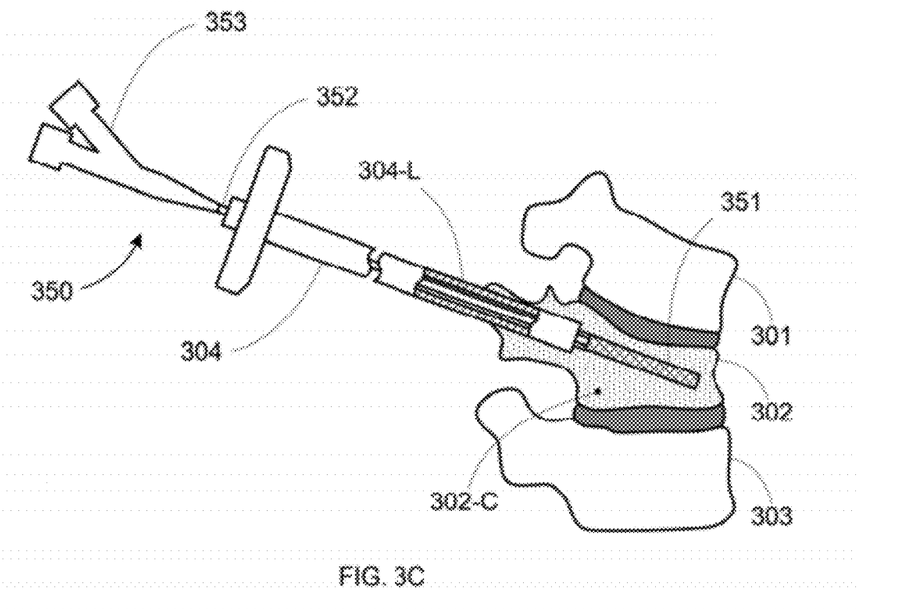

Then in FIG. 3C, a cavity creation device 350 is placed into cannula 304. For exemplary purposes, cavity creation device 350 is depicted and described as an inflatable bone tamp, but in various other embodiments, cavity creation device 350 can be any device capable of forming a void within cancellous bone 302-C of vertebral body 302 (e.g., a mechanical cavity creation device (e.g., stent, tamp, whisk, osteotome, or curette) or an energy delivery system (e.g., laser, plasma, or ultrasound device), among others).

Figure 3D:
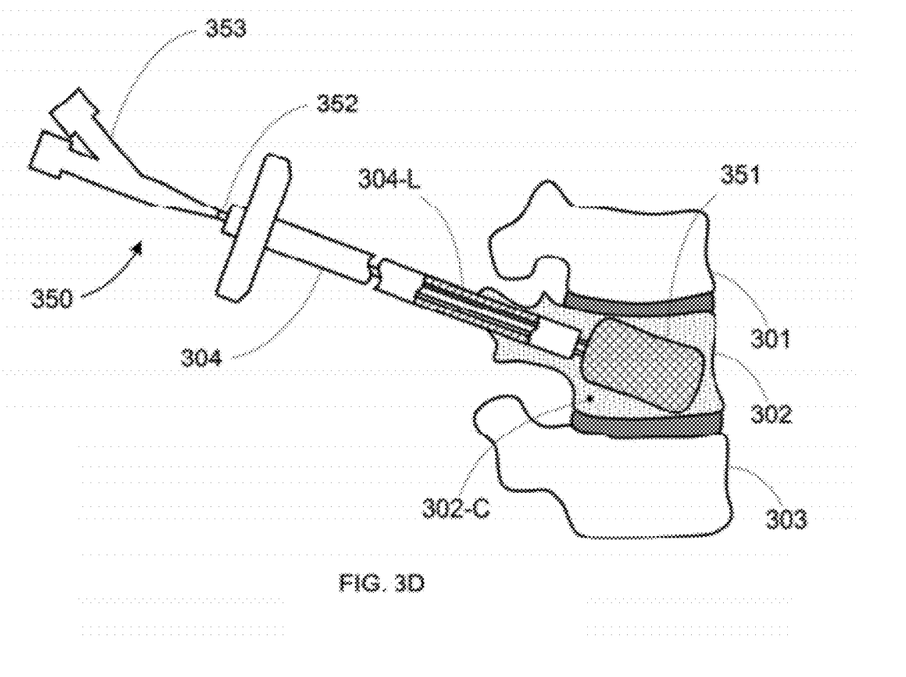

Cavity creation device 350 includes a shaft 352 (e.g., a catheter), an inflatable structure 351 (e.g., a balloon) at the distal end of shaft 352, and a connector 353 (e.g., a Luer Lock fitting) at the proximal end of shaft 352. Inflatable structure 351 can therefore be inflated within cancellous bone 302-C, as shown in FIG. 3D. This inflation can be performed by any system (not shown for clarity) capable of delivering an inflation fluid (e.g., saline or contrast solution) to inflatable structure 351 (e.g., a syringe, pump, or pressurized system, among others).

As inflatable structure 351 expands to compress cancellous bone 302-C, it pushes apart the cortical bone endplates of vertebral body 302, which can result in partial or complete height restoration of vertebral body 302. Once inflatable structure 351 has been expanded to a desired volume and/or a desired height restoration has been achieved in vertebra 302, inflatable structure 351 is deflated and cavity creation device 350 is removed from cannula 304.

Figure 3E:
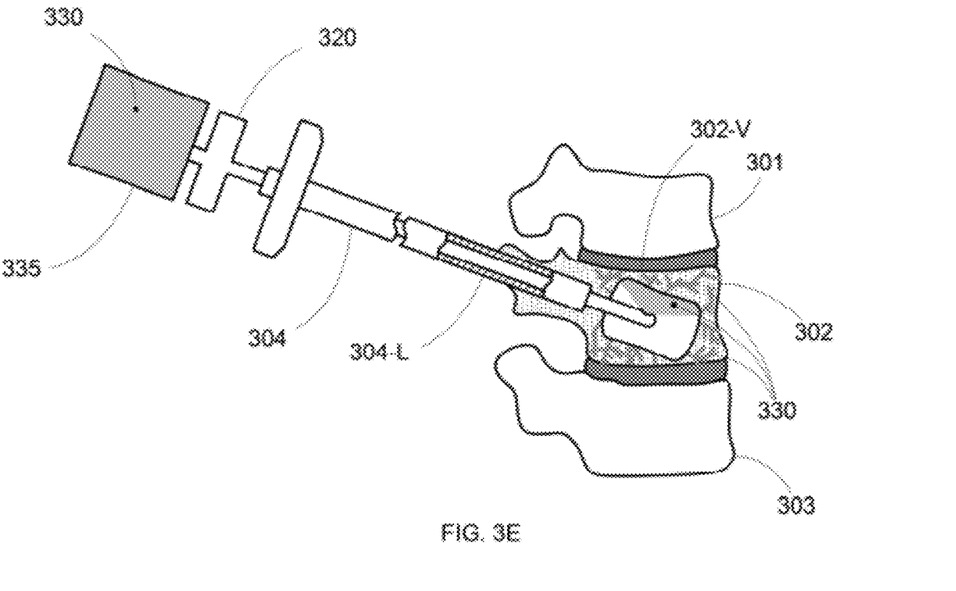

The resulting cavity 302-V formed within cancellous bone 302-C shown in FIG. 3E provides a space into which bone cement can be delivered. The compacted cancellous bone 302-C can create a barrier to contain that bone cement, but may not fully block all possible cement extravasation paths.

Therefore, a delivery nozzle 320 can be positioned in cavity 302-V via cannula 304, and a delivery system 335 coupled to delivery nozzle 320 can then be used to deliver a calcium-dependent polymerizing sealant 330 (similar to sealants 130 and 230 described with respect to FIGS. 1A-1D and FIGS. 2A-2D, respectively, such as a sealant including sodium alginate) to vertebral body 302.

Sealant 330 flows into vertebral body 302, filling cracks and crevices within the cancellous bone 302-C and/or the cortical bone of vertebral body 302. Specifically, the calcium within vertebral body 302 causes sealant 330 to polymerize and stiffen, and thereby provide the desired gap-filling within vertebral body 302.

Note that delivery system 335 can be any system for delivering sealant 330, including a syringe, a high pressure injection system (e.g., hydraulic pump, pressurized system, mechanical linkages/screw system), and/or automated feed systems, among others.

Note further that delivery nozzle 320 can be any structure for conveying sealant 330 to vertebral body 302. Although delivery nozzle 320 is depicted as providing directional delivery (e.g., spraying) of sealant 330 within cavity 302-V for exemplary purposes, in various other embodiments, delivery nozzle 320 can provide any type of delivery profile (e.g., omnidirectional, tip-based dispensing, fenestrated dispensing, or any other delivery mechanism for either high-pressure or low pressure delivery).

Figure 3F:
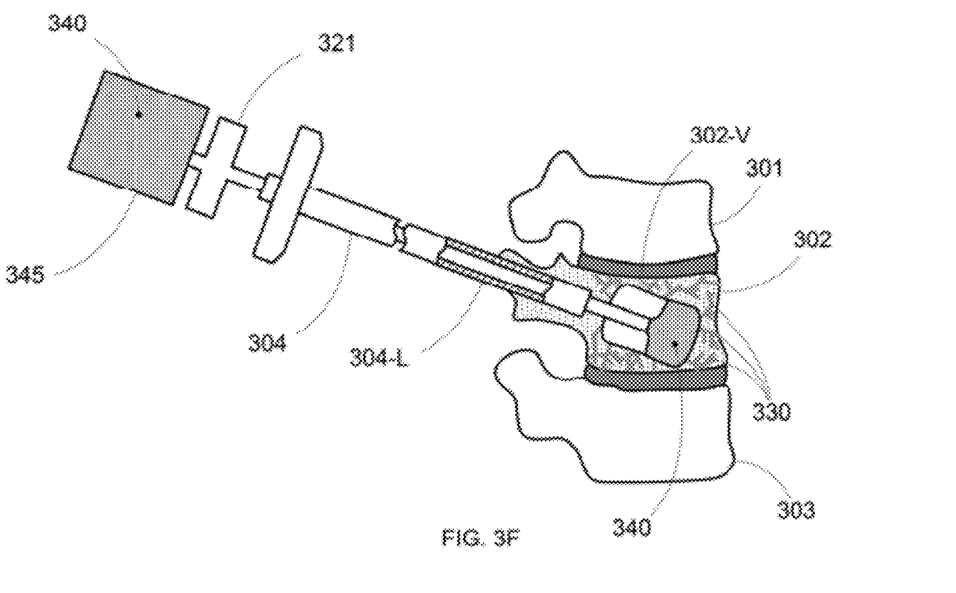

Once the desired sealing of vertebral body 302 has been achieved, bone cement 340 can be delivered into vertebral body 302, as shown in FIG. 3F. In particular, a delivery nozzle 321 can be positioned within cavity 302-V via cannula 304, and a delivery system 345 can be coupled to delivery nozzle 321 to urge bone cement 340 into cavity 302-V. Delivery system 345 can be any system for delivering bone cement 340 through delivery nozzle 321 into vertebral body 302, such as a syringe, a high pressure injection system (e.g., hydraulic pump, pressurized system, mechanical linkages/screw system), and/or automated feed systems, among others.

In some embodiments, delivery system 345 can be the same as delivery system 335 (e.g., the same high pressure injection system but coupled to a reservoir of bone cement 340, or a two-chamber syringe, among others). In various other embodiments, delivery system 345 can be a separate (and optionally different) delivery system (e.g., a syringe for the lower viscosity sealant 330 and a high pressure injection system for the higher viscosity bone cement 340).

Note that in some embodiments, delivery nozzles 320 and 321 can be the same instrument, such that delivery systems 335 and 345 deliver sealant 330 and bone cement 340, respectively, through the same delivery nozzle. In other embodiments, different delivery nozzles 320 and 321 can be used with delivery systems 335 and 345, respectively. Note further that in various other embodiments, bone cement 340 can be delivered in multiple portions of the same or different materials (e.g., a bone cement followed by a biologic agent).

Figure 3G:
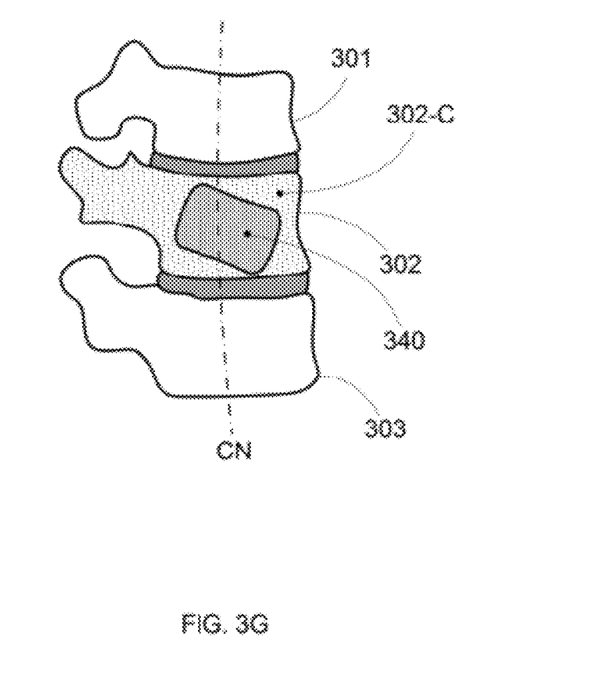

In any event, because cracks and other potential external passageways in vertebral body 302 have been filled by sealant 330, bone cement 340 can be largely contained within cavity 302-V, thereby minimizing the risk of bone cement extravasation. Once a desired amount of bone cement 340 is delivered into vertebral body 302, delivery nozzle 321 and cannula 304 are removed from vertebra 302 (and the patient's body) as shown in FIG. 3G.

Upon hardening, bone cement 340 provides structural support for vertebra 302, thereby substantially restoring the structural integrity of the bone and the proper musculoskeletal alignment of the spine. As shown in FIG. 3G, due to the restoration of height in fractured vertebra 302, the abnormal curvature CK shown in FIG. 3A is corrected to a normal curvature CN. In this manner, the pain and attendant side effects of a vertebral compression fracture can be addressed by a minimally invasive kyphoplasty procedure.

To facilitate the above-described procedure, in some embodiments, a kyphoplasty kit can be provided that includes cannula 304, cavity creation device 350, delivery nozzle 320, a quantity of sealant 330, and instructions for using sealant 330 with delivery nozzle 320. In various other embodiments, the kit can include additional hardware/instruments, such as guidewires, drills, drivers, delivery systems, and/or bone cement.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The invention claimed is:

1. A method for treating a bone structure, comprising:
    providing a kit comprising:
        a calcium-dependent polymerizing sealant comprising an alginate,
        a high pressure injection system for delivering the calcium-dependent polymerizing sealant,
        bone cement,
        a second injection system for delivering the bone cement, and
        instructions for use of the kit;
    injecting the calcium-dependent polymerizing sealant into the bone structure;
    allowing the calcium-dependent polymerizing sealant to polymerize in the bone structure; and
    injecting the bone cement into the bone structure, wherein the calcium-dependent polymerizing sealant is injected into the bone structure before the bone cement is injected into the bone structure to prevent bone cement extravasation.

2. The method of claim 1, wherein at least one of the high pressure injection system and the second injection system comprises a bone screw, the bone screw extending along a longitudinal axis between a first end and an opposite second end, the bone screw comprising an inner surface defining a passageway extending along the longitudinal axis, the passageway comprising a first opening at the first end and a second opening at the second end, the bone screw further comprising a plurality of spaced apart fenestrations extending through the inner surface and an opposite outer surface of the bone screw, the fenestrations being in communication with the passageway.

3. The method of claim 1, wherein the bone structure comprises a vertebral body, wherein the high pressure injection system comprises a needle, and wherein the needle is used to inject the calcium-dependent polymerizing sealant into the vertebral body.

4. The method of claim 3, wherein the needle is flexible.

5. The method of claim 1, wherein the bone structure comprises a vertebral body, wherein at least one of the high pressure injection system and the second injection system comprises a cannula, a cavity creation device and a delivery device, and wherein:
    the cannula is configured for establishing an access path to the vertebral body;
    the cavity creation device is configured for creating a cavity within the vertebral body through the cannula; and
    the delivery device is a delivery nozzle sized to fit through the cannula for delivering the calcium-dependent polymerizing sealant and the bone cement into the cavity.

6. The method of claim 1, wherein the alginate is sodium alginate.

7. The method of claim 1, wherein at least one of the high pressure injection system and the second injection system comprises a syringe, the syringe comprising a first chamber and a second chamber, the calcium-dependent polymerizing sealant being disposed in the first chamber prior to being injected into the bone structure and the bone cement being disposed in the second chamber prior to being injected into the bone structure.

8. The method of claim 1, wherein the high pressure injection system and the second injection system each comprise a hydraulic pump.

9. The method of claim 1, wherein the high pressure injection system and the second injection system each comprise a syringe.

10. The method of claim 1, wherein the high pressure injection system comprises a hydraulic pump and the second injection system comprises a manual syringe.

11. A method comprising:
    providing a kit comprising:
        at least one bone screw, bone cement,
a high pressure injection system for delivering the bone cement,
a calcium-dependent polymerizing sealant consisting of an alginate,
a second high pressure injection system for delivering the calcium-dependent polymerizing sealant,
an injection consisting of calcium, and
instructions for use of the kit;
injecting the calcium-dependent polymerizing sealant into a bone structure;
allowing the calcium-dependent polymerizing sealant to polymerize in the bone structure; and
injecting the bone cement into the bone structure,
wherein the calcium-dependent polymerizing sealant is injected into to the bone structure before the bone cement is injected into the bone structure to prevent bone cement extravasation.

12. The method of claim 11, wherein the alginate is sodium alginate.

13. A method comprising:
providing a kit comprising:
bone cement,
a high pressure injection system for delivering the bone cement,
a calcium-dependent polymerizing sealant comprising sodium alginate,
a second high pressure injection system for delivering the calcium-dependent polymerizing sealant, and
instructions for use of the kit;
injecting the calcium-dependent polymerizing sealant into a bone structure;
allowing the calcium-dependent polymerizing sealant to polymerize in the bone structure; and
injecting the bone cement into the bone structure,
wherein the calcium-dependent polymerizing sealant is injected into the bone structure before the bone cement is injected into the bone structure to prevent bone cement extravasation.

14. The method of claim 13, wherein the calcium-dependent polymerizing sealant comprises a calcium injection.

15. The method of claim 13, wherein the bone cement has a viscosity which is higher than that of the calcium-dependent polymerizing sealant.

16. The method of claim 13, wherein:
the second high pressure injection system includes a manual syringe that is used to inject the calcium-dependent polymerizing sealant into the bone structure; and
the first high injection system includes a hydraulic pump that is used to inject the bone cement into the bone structure.

17. The method of claim 13, wherein the kit comprises a bone screw, the bone screw comprising a threaded shaft, a passageway that extends through the shaft and fenestrations that are in communication with the passageway, and wherein injecting the calcium-dependent polymerizing sealant into the bone structure comprises disposing the high pressure injection within the passageway to deliver the calcium-dependent polymerizing sealant to the bone structure through the fenestrations.

18. The method of claim 13, wherein the first high injection system includes a manual syringe that is used to inject the bone cement into the bone structure and the second high pressure injection system comprises a hydraulic pump.

* * * * *

UNITED STATES PATENT AND TRADEMARK OFFICE
CERTIFICATE OF CORRECTION

PATENT NO. : 9,549,760 B2  
APPLICATION NO. : 12/915540  
DATED : January 24, 2017  
INVENTOR(S) : Steele Page 1 of 1

It is certified that error appears in the above-identified patent and that said Letters Patent is hereby corrected as shown below:

On the Title Page

In Item (57), under "ABSTRACT", in Column 2, Line 1, delete "extravaation" and insert -- extravasation --, therefor.

In Item (57), under "ABSTRACT", in Column 2, Line 7, delete "extravaation." and insert -- extravasation. --, therefor.

Signed and Sealed this  
Twenty-sixth Day of September, 2017

Joseph Matal  
*Performing the Functions and Duties of the*  
*Under Secretary of Commerce for Intellectual Property and*  
*Director of the United States Patent and Trademark Office*